(12) United States Patent
Yousfi et al.

(10) Patent No.: US 11,594,319 B2
(45) Date of Patent: Feb. 28, 2023

(54) SYSTEMS AND METHODS FOR MANAGING, VALIDATING, AND TRANSMITTING HEALTH DATA ACROSS GEOGRAPHIC REGIONS

(71) Applicant: HeartFlow, Inc., Redwood City, CA (US)

(72) Inventors: Razik Yousfi, Redwood City, CA (US); Leo Grady, Redwood City, CA (US); Jay Sastry, Redwood City, CA (US)

(73) Assignee: HeartFlow, Inc., Redwood City, CA (US)

( * ) Notice: Subject to any disclaimer, the term of this patent is extended or adjusted under 35 U.S.C. 154(b) by 278 days.

(21) Appl. No.: 16/797,678

(22) Filed: Feb. 21, 2020

(65) Prior Publication Data

US 2020/0273558 A1 Aug. 27, 2020

Related U.S. Application Data

(60) Provisional application No. 62/809,151, filed on Feb. 22, 2019.

(51) Int. Cl.
*G16H 30/20* (2018.01)
*G16H 10/60* (2018.01)
*G16H 15/00* (2018.01)
*G16H 50/20* (2018.01)
*G16H 80/00* (2018.01)

(52) U.S. Cl.
CPC ............. *G16H 30/20* (2018.01); *G16H 10/60* (2018.01); *G16H 15/00* (2018.01); *G16H 50/20* (2018.01); *G16H 80/00* (2018.01)

(58) Field of Classification Search
CPC ........ G16H 30/20; G16H 10/60; G16H 15/00; G16H 80/00; G16H 50/20; G06F 9/547
USPC .......................................... 705/2–4
See application file for complete search history.

(56) References Cited

U.S. PATENT DOCUMENTS

| 7,552,482 | B2 * | 6/2009 | Redlich | ............... | G06F 21/6209 715/255 |
| 2004/0139222 | A1 * | 7/2004 | Slik | ......................... | G16H 10/60 709/236 |
| 2009/0254572 | A1 * | 10/2009 | Redlich | ................ | G06Q 10/107 |
| 2010/0122336 | A1 * | 5/2010 | Hunt | ....................... | H04L 67/26 726/11 |

(Continued)

OTHER PUBLICATIONS

International Search Report and Written Opinion issued in International Application PCT/US2020/019246, dated May 22, 2020.

*Primary Examiner* — Mark Holcomb
(74) *Attorney, Agent, or Firm* — Bookoff McAndrews, PLLC

(57) ABSTRACT

Systems and methods are disclosed for preserving patient privacy while allowing health data to be analyzed, managed, and stored in different geographical areas. One method for managing cross-border health data while preserving patient privacy includes: receiving a DICOM object from a hospital computing device for analysis; generating a unique case identifier for the DICOM object; validating the received DICOM object; if, based on the validation, the received DICOM object is valid, anonymizing the received DICOM object; updating the anonymous DICOM object to include the unique case identifier; compressing the updated DICOM object; and sending the compressed DICOM object to at least one data analysis web service(s).

20 Claims, 10 Drawing Sheets

(56) References Cited

U.S. PATENT DOCUMENTS

| | | | |
|---|---|---|---|
| 2016/0285852 A1* | 9/2016 | Seliger | G06F 8/61 |
| 2016/0342738 A1 | 11/2016 | Stalling et al. | |
| 2018/0137244 A1* | 5/2018 | Sorenson | G16H 30/40 |
| 2018/0152339 A1* | 5/2018 | Gunjal | H04L 41/5058 |
| 2020/0161005 A1* | 5/2020 | Lyman | G06K 9/6262 |

* cited by examiner

SYSTEMS AND METHODS FOR MANAGING, VALIDATING, AND TRANSMITTING HEALTH DATA ACROSS GEOGRAPHIC REGIONS

RELATED APPLICATION(S)

This application claims priority to U.S. Provisional Application No. 62/809,151 filed Feb. 22, 2019, the entire disclosure of which is hereby incorporated herein by reference in its entirety.

INTRODUCTION

Hospitals generate and store a significant amount of health data records relating to patients. Traditionally, health data (e.g., medical reports, X-rays, CT scans, etc.) analysis is performed by medical professionals at the hospitals. However, a hospital may not be able to perform predictive health data analysis involving cutting edge technology (e.g., involving image processing, natural language processing, and artificial intelligence). Increasingly, various aspects of health data analysis are performed outside of the hospital. When health data is analyzed outside a hospital, there may be several factors to consider for transferring the health data out of a hospital, including file size, data type, routing of data, file adequacy (e.g., image quality), Application User Interface (API) to be used to facilitate the selection of files to transfer, privacy, etc.

In certain situations, health data may need to be analyzed in a region outside of a hospital or hospital department. Various hospital facilities, departments, countries, or geographic regions may possess different requirements for protecting patient privacy. Commonly, health data may include patient privacy data, and transferring such health data outside of a designated country or region may violate patient privacy requirements. For example, United States law seeks to protect patient privacy by defining a category of information that can link an individual's health information to the individual. This category of information is called, "protected health information (PHI)," and U.S. medical professionals and service providers (e.g., doctors, hospitals, insurance companies, covered entities, business associates, etc.) are governed by regulations that dictate usage and transfer of PHI-associated health data. Other countries and regions may include analogous regulations, laws, and/or standards (e.g., GDPR).

At the same time, particular health data analysis, storage, and management capabilities may exist only within a certain region. For example, a particular medical data analysis may involve usage of web services and an infrastructure involving analyses available only in one selected region. Patients outside of that selected region may not have access to the analysis services, since patient privacy regulations may dictate that their patient privacy information (and thus their health data) cannot be transferred to the selected region. In short, patient privacy regulations limiting cross-border transfer of patient privacy information may mean that data cannot be analyzed by data analysis facilities that exist out of region. Consequently, patients may be limited to data analysis capabilities available within certain regions.

A desire thus exists for a health data management system that may create a secure, scalable, robust, elastic infrastructure for the end-to-end automated ingestion and processing of health data in preparation for out-of-region analysis. A desire further exists for a health data management system capable of providing reports comprising the analyzed health data results of out-of-region analysis. In one embodiment, various systems and methods of the health data management system may include a guided analyst workflow for validating results of the out-of-region analysis.

The foregoing general description and the following detailed description are exemplary and explanatory only and are not restrictive of the disclosure. Various embodiments of the present disclosure relate to systems and methods that preserve patient's privacy while efficiently analyzing, managing, and storing health data in different geographical areas, according to one embodiment.

SUMMARY

According to certain aspects of the present disclosure, systems and methods are disclosed for managing cross-border health data for analysis, while preserving patient privacy.

A method of managing cross-border health data while preserving patient privacy, the method includes: receiving a DICOM object from a hospital computing device for analysis; generating a unique case identifier for the DICOM object; validating the received DICOM object; if, based on the validation, the received DICOM object is valid, anonymizing the received DICOM object; updating the anonymous DICOM object to include the unique case identifier; compressing the updated DICOM object; and sending the compressed DICOM object to at least one data analysis web service(s).

In accordance with another embodiment, a system for managing cross-border health data while preserving patient privacy comprises: a data storage device storing instructions for managing cross-border health data while preserving patient privacy; and a processor configured for: receiving a DICOM object from a hospital computing device for analysis; generating a unique case identifier for the DICOM object; validating the received DICOM object; if, based on the validation, the received DICOM object is valid, anonymizing the received DICOM object; updating the anonymous DICOM object to include the unique case identifier; compressing the updated DICOM object; and sending the compressed DICOM object to at least one data analysis web service(s).

In accordance with another embodiment, a non-transitory computer readable medium for use on a computer system containing computer-executable programming instructions for performing a method of managing cross-border health data while preserving patient privacy, the method comprising: receiving a DICOM object from a hospital computing device for analysis; generating a unique case identifier for the DICOM object; validating the received DICOM object; if, based on the validation, the received DICOM object is valid, anonymizing the received DICOM object; updating the anonymous DICOM object to include the unique case identifier; compressing the updated DICOM object; and sending the compressed DICOM object to at least one data analysis web service(s).

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

DESCRIPTION OF THE EMBODIMENTS

Figure 1:
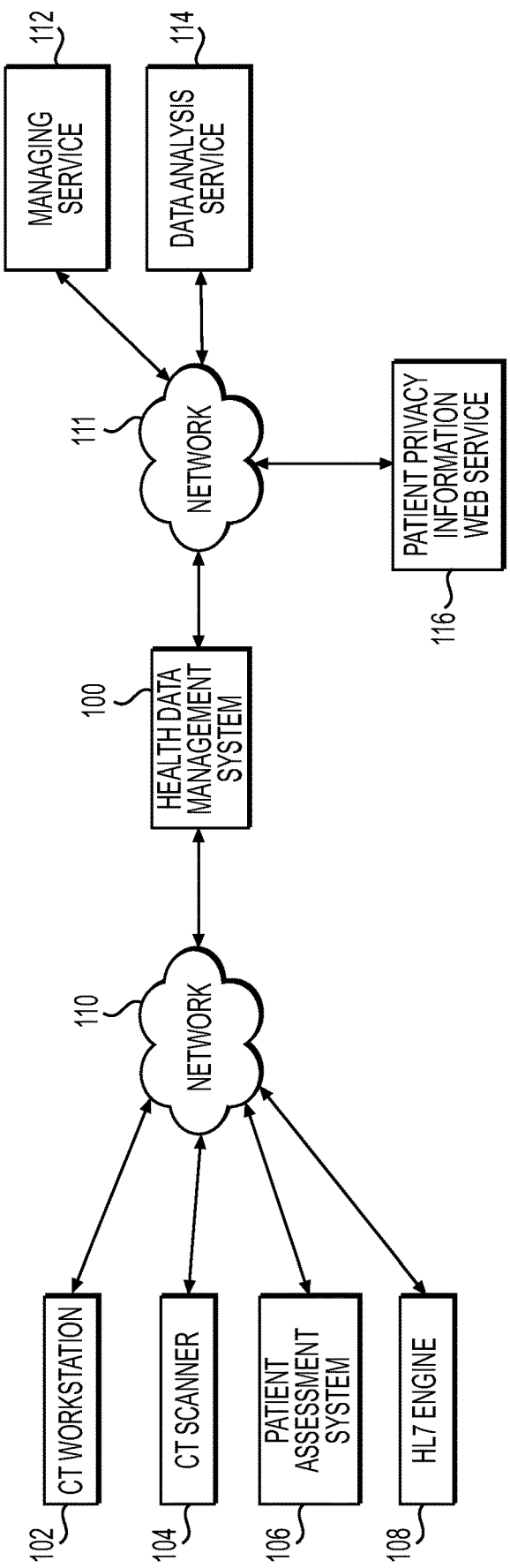
FIG. 1 depicts an exemplary schematic block diagram of health data management between hospital(s) and data analysis vendor(s), according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

As used herein, the term "exemplary" is used in the sense of "example," rather than "ideal." Moreover, the terms "a" and "an" herein do not denote a limitation of quantity, but rather denote the presence of one or more of the referenced items. For the purposes of the disclosure, "patient" may refer to any individual or person for whom diagnosis or treatment analysis (e.g., data analysis) is being performed, or any individual or person associated with the diagnosis or treatment analysis of one or more individuals.

The term, "health data" may include medical data (e.g., Digital Imaging and Communications in Medicine (DICOM) objects) collected for a patient in one practice, as well as health data collected for the patient by any health care providers, labs, specialists, clinicians, etc. Health data may be associated with a particular patient, where the patient is identifiable via patient privacy information. Patient privacy information may be any information that links health data to a particular individual. Patient privacy information may be defined objectively (as information that ties an individual to his/her health data) and/or by laws and regulations. Various regions may include different definitions of what information that constitutes patient privacy information.

"Region" may refer to any environment with borders defined by regulations protecting patient privacy. In one embodiment, "region" may refer to a known geographic region governed by a set of regulations that protect patient privacy/personal data. For example, "region" may refer to a state (e.g., California), a country (e.g., the United States, Japan, Canada, etc.), or a group of countries (e.g., Europe) operating under a single set of patient privacy laws. For the United States, patient privacy information may include protected health information (PHI). For the United States and various other regions, patient privacy information may include personal health information, patient identification information, etc. (e.g., CT, MRI, ultrasound, etc.). Various systems and methods for protecting patient health information while transmitting health data are disclosed, for example, in U.S. Non-Provisional application Ser. No. 15/635,127 filed Jun. 27, 2017 and entitled "Systems and Methods for Modifying and Reacting Health Data Across Geographic Regions," which is hereby incorporated herein by reference in its entirety.

Alternately or in addition, "region" may refer to a given physical facility, a given entity's computing systems, or a given cloud platform. In such cases, various regions between which health data is redacted may nevertheless exist within a single country, state, or province. For example, a region may include a hospital that may remove patient privacy information from collected health data prior to transferring the health data to another region (e.g., a cloud platform) for data analysis. The hospital and the cloud platform may exist in the same geographically defined region, e.g., the United States.

The present disclosure includes a system and method for transferring health data out of a hospital. In one embodiment, the health data may be transferred to a cloud-based web service for analysis. The health data transfer may include selecting or identifying files to transfer for analysis, preparing the files for transfer or for analysis, performing automatic health data ingestion, timing the transfer of file(s), determining whether various files are related, detecting completed analyses of health data, monitoring the status or progress of health data analysis, generating reports of completed analyses, receiving or transmitting reports of completed analyses, and otherwise managing the interactions between a region (e.g., a hospital) and the cloud-based web service.

In one embodiment, preparing files for transfer and determining completed analyses may involve preserving patient privacy during the transfer of health data out of a first region. In an exemplary case, a first region may include a hospital. In such a scenario, a health data management system may include one embodiment of transferring data out of hospitals to vendors for remote analysis of the data. In one embodiment, the health data management system may receive health data from a hospital, where the file of health data includes patient privacy information. The health data management system may anonymize the health data file by stripping patient privacy information from the health data. The health data management system may further send anonymous health data to a cloud-based data analysis web service. In one embodiment, patient privacy information may be sent and stored in a region-specific cloud-based web service (e.g., at the first, hospital region). In other words, the anonymized health data may be transferred out of the first region to a cloud-based data analysis web service, while patient privacy information associated with the health data may remain in the first region at the region-specific cloud-based web service.

In one embodiment, the health data management system may generate or detect completed report(s) comprising results of health data analysis from the cloud-based data analysis web service. In one embodiment, the health data management system may push result report(s) to a region (e.g., the first, hospital region). In this way, data analysis may be performed in a remote region, without transmitting patient privacy information to the remote region. In other words, transmission of health data may include modifying and redacting patient privacy information from the health data so that the health data may undergo analysis at a remote region while preserving patient privacy.

In one embodiment, the health data management system may transfer health data (e.g., DICOM objects) from customer sites (e.g., hospitals, clinics, etc.) to cloud computing web-service(s) for analysis of the DICOM objects. The system may receive health data directly from CT scanner(s), CT workstation(s), or a patient assessment system using DICOM protocol.

In one embodiment, the health data may include patient-specific image data (e.g., in the form of DICOM files). In one scenario, image data may include data regarding the geometry of a patient's heart, e.g., at least a portion of the patient's aorta, a proximal portion of the main coronary arteries (and the branches extending therefrom) connected to the aorta, and/or the myocardium. Patient-specific anatomical data may be obtained noninvasively, e.g., using a non-invasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart.

Alternatively, other noninvasive imaging methods (including magnetic resonance imaging (MRI) or ultrasound (US)) or invasive imaging methods (such as digital subtraction angiography (DSA)) may be used to produce images of structures of a patient's anatomy. The imaging methods may involve injecting the patient intravenously with a contrast agent to enable identification of the structures of the anatomy. The health data involving images (e.g., generated by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may include blood pressure in the patient's brachial artery (e.g., using a pressure cuff), such as the maximum (systolic) and minimum (diastolic) pressures. Exemplary health data may thus include data collected from imaging modalities, wearables, blood pressure cuffs, thermometers, fitness trackers, glucometers, heart rate monitors, etc.

FIG. 1 is a schematic block diagram of a hospital-vendor system for managing health data via cloud platforms, according to an exemplary embodiment of the present disclosure. A hospital-vendor system may comprise a health data management system 100 configured to receive information from hospital computing device(s) (CT workstation 102, CT scanner 104, patient assessment system 106, etc.) over a wireless network 110. In one embodiment, wireless network 110 may include a network local to a hospital network (e.g., a first region), and the health data management system 100 may be deployed in wireless network 110. In one embodiment, the hospital may be a site that is enrolled as a customer of a vendor. An exemplary vendor of the hospital-vendor system may include a data analysis service (e.g., data analysis service 114).

In one embodiment, health data management system 100 may be deployed in the hospital network as a virtual appliance delivered as a single file on wireless network 110. For example, a site administrator of the hospital may download a file containing the health data management system 100 from a vendor user interface. The download may enable hospital computing device(s) (CT workstation 102, CT scanner 104, patient assessment system 106, etc.) to move DICOM studies to the virtual machine (e.g., health data management system 100). In one embodiment, the site administrator also enrolls the hospital as a customer of the vendor, thus connecting the health data management system 100 also to the network of the vendor (e.g., network 111 of a data analysis service 114). These processes are described in more detail at FIG. 8A-8C.

In an example embodiment, the health data management system 100 may query hospital computing device(s) such as (CT workstation 102, CT scanner 104, and patient assessment system 106) and pull one or more DICOM objects from such computing device(s). In an example embodiment, a DICOM object may include patient privacy information, priority level of an analysis to be performed on file(s) of the DICOM object, a type of case study/analysis to be conducted, patient scan/images, etc. Alternately or in addition, a hospital computing device may be connected to a web server that serves or saves DICOM objects. In such a case, the health data management system 100 may pull one or more DICOM objects from the server. In yet another embodiment, the DICOM objects may be uploaded (e.g., to a data analysis service 114) using a web interface provided by the health data management system 100. In short, the health data management system 100 may receive health data files via a network of a first region (e.g., network 110 of a hospital) and upload health data files to a data analysis service 114 at a second region using various methods (e.g., over network 111). As previously described, health data management system 100 may anonymize health data file(s) before uploading the files out of the first region (e.g., by removing patient privacy information from the health data file(s)).

In one embodiment, managing service(s) 112 may manage the subscriptions/customers of data analysis service(s) 114. For example, managing service(s) 112 may enroll one or more customers of vendors that analyze anonymous health data. For instance, managing service(s) 112 may receive requests from prospective customers (e.g., hospitals) wishing to have the services provided by data analysis service(s) 114. In one scenario, managing service(s) 112 may serve as one or more cloud platform(s) for managing and storing anonymous health data. Managing service(s) 112 may provide, to the hospitals, an interface for providing anonymous health data to the data analysis service(s) 114. In one embodiment, the interface may be the health data management system 100, which may convert hospital-generated health data to anonymous health data and route the data to the appropriate data analysis web service(s).

In one embodiment, managing service(s) 112 may further manage the order in which health data files are analyzed by data analysis service(s) 114. In one embodiment, the order may be based on the order in which the files were generated, uploaded, and/or a priority level associated with each of the files. The managing service(s) 112 may further generate, manage, and store report(s) for the analyzed anonymous health data. For example, the managing service(s) 112 may vary reports generated, depending on the customer (e.g., hospital) where the DICOM object originated. For example, various customers may configure various settings during enrollment. The reports may be generated based on settings dictated at enrollment. In one embodiment, the health data management system 100 and/or managing service(s) 112 may manage anonymous health data file(s) and/or reports.

The data analysis service(s) 114 may comprise a web service and serve as one or more cloud platform(s) for analyzing anonymous health data. Additionally, the data analysis service(s) 114 may compute results and generate result reports (e.g., 3D model, PDF, etc.) to present analysis and results to a hospital user. For example, one or more web service(s) of the data analysis service(s) 114 may compute blood flow within coronary arteries using received anonymous health data from cardiac CT scans of hospital computing device(s). The one or more web service(s) may provide an interactive 3D model of the coronary arteries showing computed Fractional Flow Reserve values along with a PDF report.

In one embodiment, a patient privacy information web service 116 may serve as one or more cloud platform(s) for managing and storing patient privacy information. The patient privacy information web service 116 may pair patient privacy information with completed reports from data analysis service(s) 114. For example, health data management system 100 may store patient privacy information in a database, using patient privacy information web service 116. In this way, patient privacy information may be isolated from data analysis service(s) 114. In one embodiment, patient privacy information web service 116 may re-identify anonymous reports from data analysis service(s) 114 by pairing the reports with stored patient privacy information of a database of or accessibly by the patient privacy information web service 116. In one embodiment, a patient privacy information web service 116 may only be accessible from the region where the health data was generated (e.g., network 110). In another embodiment, patient privacy information web service 116 may be prompted by the health data management system 100 to provide identification information to completed reports (e.g., over network 111). In some cases, the patient privacy information web service 116 may provide identification information devoid of patient privacy information.

Network 110 and network 111 may include the Internet, a content distribution network, or any other wired, wireless, and/or telephonic or local network. In one embodiment, health data management system 100, CT scanner 104, CT workstation 102, patient assessment system 106, and HL7 engine 108 may communicate with each other via network 110. For example, the health data management system 100 may receive health data (e.g., DICOM objects) from the CT scanner 104, CT workstation 102, or patient assessment system 106 over network 110. The health data management system 100 may further transmit completed reports, notifications of completed reports, or hindrances to completing reports (e.g., health data quality issues) to the CT scanner 104, CT workstation 102, or patient assessment system 106 over network 110. Health data management system 100 may further push the completed reports to the patient privacy information web service 116 over network 110 or network 111, so that reports from the data analysis service 114 may be paired with patient privacy information.

The health data management system 100 may also be configured to communicate with managing service 112 and data analysis service 114 over a wireless network 111. For instance, the health data management system 100 may upload raw health data to a data analysis service 114 for analysis. The health data management system 100 may also communicate with the managing service 112 to receive data logs indicating the status or progress of an analysis. Further, the health data management system 100 and/or managing service 112 may receive or push analysis report(s) (e.g. PDF results) from the data analysis service 114 via network 111, and convey the reports to various interfaces that are part of network 110. Managing service 112 and data analysis service 114 may also communicate over wireless network 111.

Figure 2:
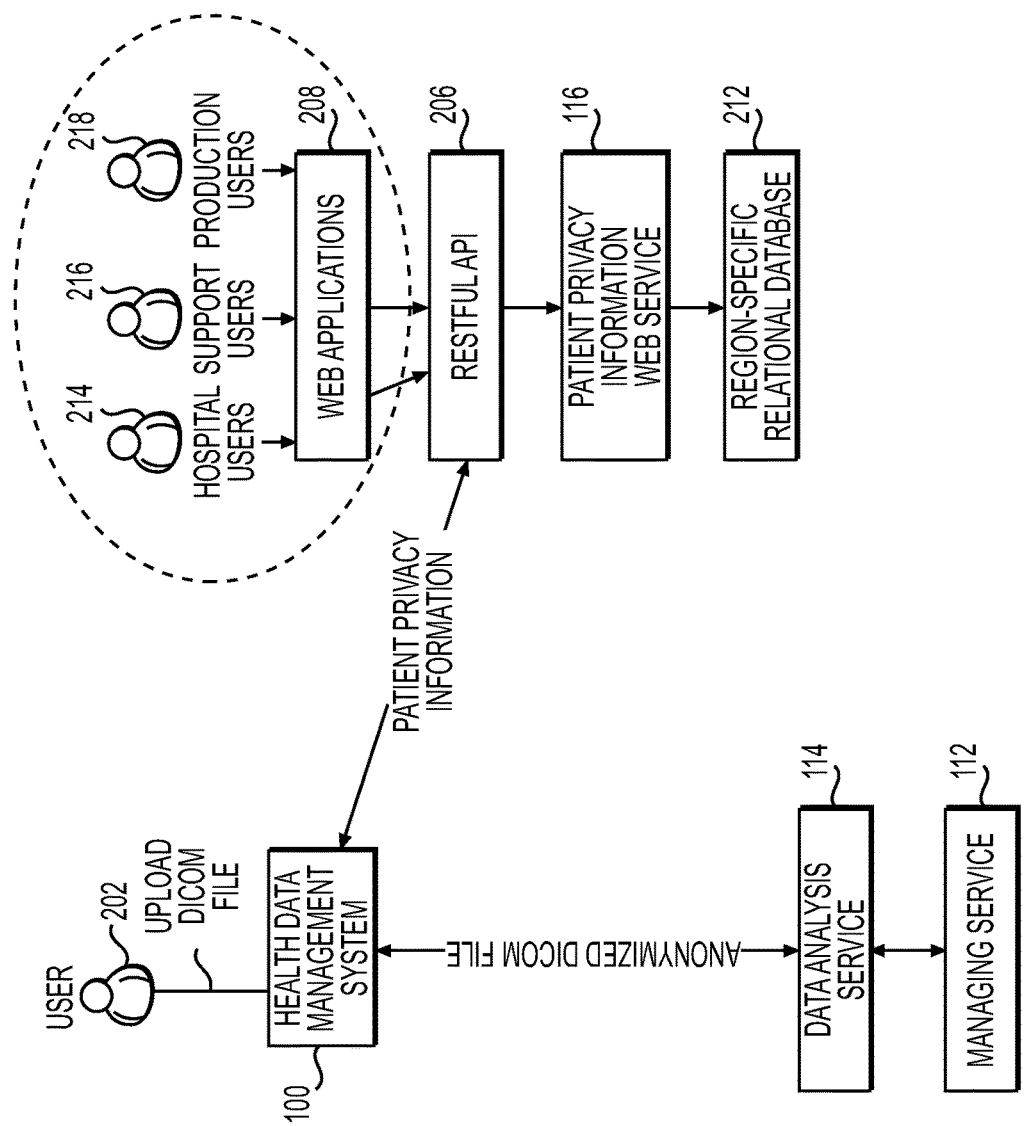
FIG. 2 depicts an exemplary dataflow of the health data through the health data management system 100 of FIG. 1, according to an exemplary embodiment of the present disclosure.

FIG. 2 depicts an exemplary detailed diagram of the interaction between the health data management system 100 and a patient privacy cloud platform (e.g., the patient privacy information web service 116) of FIG. 1, according to an exemplary embodiment of the present disclosure. Any platform or service built to store data may be employed as the patient privacy cloud platform. The storage of patient privacy information comprising PHI data is one exemplary embodiment of the present disclosure.

In one embodiment, a user 202 may upload a DICOM object from hospital computing device(s) (e.g., CT workstation, CT Scanner, patient assessment system, etc.). Once the health data management system 100 receives the uploaded DICOM object, the health data management system 100 may extract patient privacy information (e.g., PHI data) from the DICOM object. The patient privacy information may be sent to a region-specific cloud platform (e.g., patient privacy information web service 116) using a service that may permit stateless operations. For example, the patient privacy information may be sent to patient privacy information web service 116 via Representational State Transfer (REST) Application Programming Interface (API) 206. The API 206 may correspond to a data analysis service 114, and the API 206 may be installed at the first (e.g., hospital) region. In one scenario, patient privacy information transfer from the health data management system 100 to patient privacy information web service 116 may be performed using the Hypertext Transfer Protocol (HTTP).

In one embodiment, the patient privacy information web service 116 may include or be in communication with a database (e.g., region-specific relational database 212). For example, the patient privacy information web service 116 may receive, transfer, or access patient privacy information stored in region-specific relational database 212. A relational database may include region-specific database structured to recognize relations among stored items of information. In one embodiment, the region-specific relational database 212 may store patient privacy information extracted from DICOM objects by health data management system 100. The patient privacy information may be at-rest and encrypted in relational database 212. In an example embodiment, relational database 212 may offer encryption when a new object (e.g., received patient privacy information) is stored or accessed.

In one embodiment, all of the components illustrated in FIG. 2 may exist in a first region (e.g., a hospital network), or as part of a support service network. Accordingly, the data (e.g., of relational database 212) may remain in the first region in which the hospital computing device (e.g. the device used by user 202 to upload DICOM) is located. In one embodiment, patient privacy information may not be accessed outside of the region in which it has been stored. For example, a user who submitted a case in Japan, and travelling to a different geographical region would not be able to retrieve patient privacy information.

The hospital users 214 may interact with web application(s) 208 to review uploaded object files, review the status of case processing, update data analysis priority of case processing, etc. In other words, hospital users 214 may have access to patient privacy information and/or analyzed data from data analysis service 114 using web application(s) 208 or a web interface. In one embodiment, hospital users 214 may review the status of the case processing of the data analysis service 114. For example, health data management system 100 or web application 208 may route hospital users 214 to an endpoint of managing service 112 or patient privacy information web service 116 based on their IP address, so that the users 214 may review the status of case processing.

In one embodiment, customer support personnel 216 and production users 218 of a data analysis service 114 may have access to patient privacy information, or a stored version of patient privacy information. The customer support personnel 216 and/or the production users 218 may be associated with the data analysis service 114, while not having a direct impact or access to the analyses of the data analysis service 114. In one embodiment, customer support personnel 216 may be presented with a customer service interface, which may provide the ability to log into each region individually by leveraging a Virtual Private Network (VPN) service that may be put in place exclusively for that usage. The VPN service may extend access to patient privacy information of a specific region to the customer support personnel, even when customer support is not accessing the patient privacy information from the first region. The customer service interface may be part of a web application 208. In one embodiment, production users 218 may access or edit reports of analyzed data via a production user interface. The production user interface may be part of web application 208, and it may provide the production users 218 with interfaces for reviewing, validating, or editing any intermediary report or product of an analysis.

In one embodiment, the health data management system 100 may send the DICOM object (absent patient privacy information) to a cloud platform (e.g., data analysis service 114) for data analysis. The managing service 112 may retrieve computations performed by the data analysis service 114, generate interactive view(s), 3D model(s), or PDF report file(s), and store the result files into a database.

Once a case has been processed (or health data analysis is completed), a data report may be generated and the report may be paired with patient privacy information stored in the relational database 212. For example, health data management system 100 may identify patient privacy information associated with anonymous reports received from the data analysis service 114. In an example embodiment, patient privacy information from the relational database 212 may be retrieved using the API 206.

Figure 3:
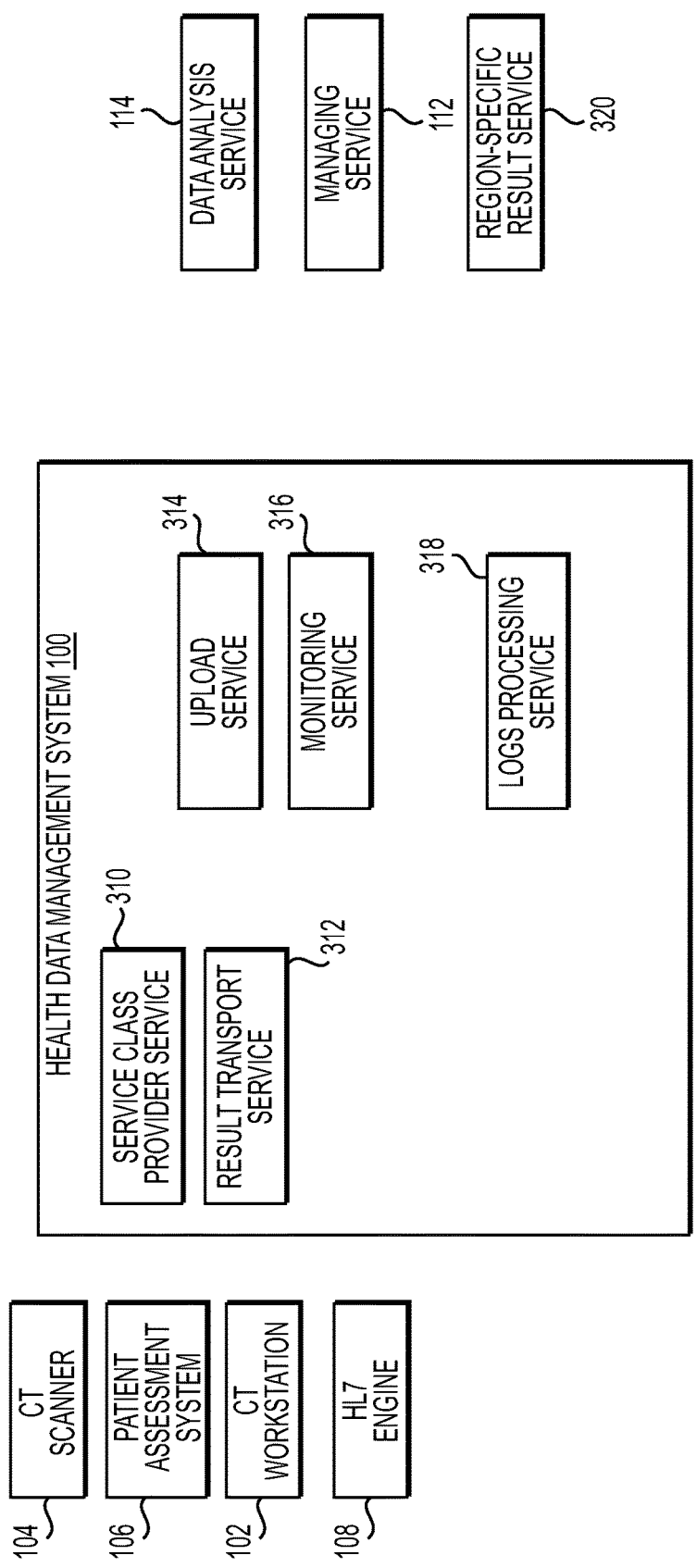
FIG. 3 depicts components of the health data management system 100 of FIG. 1, according to an exemplary embodiment of the present disclosure.

FIG. 3 depicts components of the health data management system 100 of FIG. 1, according to an exemplary embodiment of the present disclosure. Each health data management system 100 may include such an assembly of components, as described in further detail below. The health data management system 100 may be comprised of multiple web services such as a Service Class Provider (SCP) service 310, result transport service 312, upload service 314, monitoring service 316, logs processing service (e.g., logs shipper service 318), and a region-specific result service 320, as shown in FIG. 3.

In an example embodiment, a service class provider (SCP) service 310 may be part of health data management system 100, where a DICOM object from CT scanner 104, patient assessment system 106, or CT workstation 102 may be received. SCP service 310 may be implemented as a Linux service and launched after installation of the health data management system 100, e.g., at network 110. In a yet another embodiment, the SCP service 310 may be integrated with the managing service 112 through secure HTTP.

In one embodiment, the SCP service 310 may monitor one or more configured DICOM ports from a hospital computing device (e.g., CT scanner 104, patient assessment system 106, or CT workstation 102) for indications of the generation or creation of DICOM files. Once the SCP service 310 receives indication of the creation of a DICOM file by a hospital computing device, SCP service 310 may initiate creation of a case file for receiving one or more DICOM objects. For example, the SCP service 310 may create a new case and unique case identifier with managing service 112, where the new case may be identified (by the managing service 112) using the unique case identifier.

In one embodiment, SCP service 310 may receive multiple DICOM objects containing images associated with a single case study. SCP service 310 may generate a single case study involving multiple DICOM objects. In one embodiment, SCP service 310 may be configured to receive DICOM objects from one or more hospital computing devices concurrently, and SCP service 310 may generate a case file for the DICOM objects of each hospital computing device. For example, SCP service 310 may generate one case file for a set of DICOM objects received from hospital computing device "A" and a separate, second case file for a set of DICOM objects received from a different hospital computing device "B." In the above exemplary embodiment, the SCP service 310 may store a received DICOM object temporarily in a configured DICOM database.

In one embodiment, the SCP service 310 may parse one or more tags associated with received DICOM object(s). For example, the SCP service 310 may anonymize received DICOM objects. For instance, the SCP service 310 may extract the patient privacy information (e.g., PHI) from received DICOM objects, de-identify the extracted patient privacy data (e.g., by replacing the patient privacy data with a pre-defined string), and prompt storage of the patient privacy data corresponding to the received DICOM objects. In one embodiment, the DICOM object(s) may be associated with a unique case identifier that does not include patient privacy data (e.g., PHI). The data analysis service 114 and/or managing service 112 may track the DICOM object(s) using the unique case identifier. In another embodiment, parsing one or more tags associated with received DICOM object(s) may include identifying tags related to service provider(s), time, date, insurance policy, or any annotations associated with the DICOM object(s). The SCP service 310 may further process the DICOM object(s) based on the tags. For example, the SCP service 310 may provide or facilitate billing functions associated with tags related to insurance policy, time, date, or physician. As another example, the SCP service 310 may perform one or more operations on the DICOM object(s) based on annotations (e.g., from imaging acquisition). The manipulations may include assessments of image quality, reconstructions to enhance the DICOM object(s), removing or discarding files from the DICOM object(s) in order to improve image quality, etc.

In one embodiment, the SCP service 310 may compress one or more anonymous DICOM objects into one case file and upload the case file to data analysis service 114. The anonymous DICOM objects may also be uploaded to the data analysis service 114 in an uncompressed state. In a yet another embodiment, the health data management system 100 may use upload service 314 to upload the data to data analysis service 114. For example, the SCP service 310 may prompt upload service 314 when all DICOM files for a case file are received, and upload service 314 may compress the DICOM objects of a given case file and upload the compressed case file to data analysis service 114 for analysis. In one embodiment, the case file(s) may be uploaded to a data analysis service 114 that may be pre-set upon installation of the health data management system 100, or upon identifying the hospital (e.g., of CT scanner 104, patient assessment system 106, or CT workstation 102) as a customer or subscriber of data analysis service 114.

In an example embodiment, after a configured time following a successful upload, the SCP service 310 may delete the DICOM object files from storage. The configured time for deletion may be zero in an exemplary upload setting. The SCP service 310 may maintain a file system directory that reflects up-to-date status of the uploaded case study involving DICOM objects. The file system directory may keep track of new cases being received, the upload process (or the progress of uploading), and case-related error(s) (e.g., issues with uploading or issues with the files that may prevent uploading). Issues with uploading may include connectivity, network, and load issues. Issues with files may include improper file size, inadequate image quality, improper file type for the analysis requested, etc. Standards that may dictate proper files may be specific to the data analysis service 114. Further, the standards may be configured during installation of the health data management system 100.

In one embodiment, SCP service 310 may further engage in a series of operations with a hospital computing device. For example, SCP service 310 may communicate with a Service Class User (SCU) client associated with the hospital computing device. In an example embodiment, SCP service 310 may validate the identity of a hospital computing device SCU client prior to providing a connection to receive DICOM objects. In one embodiment, SCP service 310 may communicate with multiple hospital computing devices, in addition to imaging devices. The SCP service 310 may perform a set of operations unique to each of the hospital computing device(s) or unique to types of hospital computing device(s). For instance, the SCP service 310 may engage in a set of operations for a medical imaging device, and a different set of operations for a monitoring device, or a clinical testing device. For example, an operation for a medical imaging device may include a validation of image file size or type, conversion of an image file to one or more file formats, verification of completion of the imaging process, etc. An operation for a monitoring device may include time intervals for receiving data. An operation for a clinical testing device may include categorization of the test type, settings for routing the data to one or more web services or facilities for analysis, etc. The operations may be pre-set at the time of installation of the health data management system 100 on network 110. In one embodiment, the health data management system 100 may include a default set of operations associated with one or more hospital computing devices.

In an example embodiment, result transport service 312 may push result report(s) (generated by result service 320) to a pre-configured destination, e.g., a hospital web interface. The result transport service 312 may be available for configuration by a user via a (hospital) web application. In an example embodiment, the result transport service 312 may activate only if pushing of the results is "enabled" in configuration of the health data management system 100. For example, the result transport service 312 may poll a backend of a managing service 112 or database of completed analysis results for cases in a "COMPLETED" state and for PDF result reports/documents. In one embodiment, result transport service 312 may download or generate a completed report (e.g., a PDF report) that may include language settings/fields desired by users of a hospital web application. In one embodiment, the result transport service 312 may wrap the PDF document, based on configuration, either as a DICOM encapsulated PDF object or as a HL7 message and push the object to a web service of an appropriate pre-configured destination.

The logs shipper service 318 may provide periodic logs of the operations of health data management system 100. In one embodiment, an authorized user or party may request log shipment (e.g., via a remote command). In response to such a request, the logs shipper service 318 may compress and upload log files to the managing service 112. In an example embodiment, a monitoring service 316 may prompt logs shipper service 318 when it is time to transfer log files to the managing service 112. The logs shipper service 318 may compress files containing system and application log files. Such files may be stored in a database prior to sending to the managing service 112.

The monitoring service 316 may provide system upgrades for the health data management system 100. For example, monitoring service 316 may contact an Application Programming Interface (API) (e.g., API 206 of FIG. 2) at pre-set time intervals to see if a newer version of the health data management system 100 is available. The time interval may include a pre-configured update time window. If a newer version is detected, the health data management system 100 may download the appropriate files, validate their integrity, send the files to their intended destination(s), and notify the SCP service 310 of installation of an updated version of the health data management system 100. The SCP service 310 may stop accepting new connections, wait for existing jobs to finish and self-terminate. Once the SCP service 310 is no longer running, the monitoring service 316 may reboot the health data management system 100 and start the new version of the health data management system 100.

The monitoring service 316 may further send the status of the health data management system 100 to an API (e.g., API 206 of FIG. 2). The status may include the status of the SCP service 310, the number of active connections with hospital computing device(s), and the number of pending DICOM objects or cases. The monitoring service 316 may continue to report the status during the auto-update until reboot of the health data management system 100 occurs.

The monitoring service 316 may support remote commands invoked by authorized users. These commands may be issued from support users via a customer support portal. The customer support portal may send the commands to the health data management system 100 in response to the system's status report. The monitoring service 316 may execute the commands under the context of a user specifically created with limited rights just for the purpose of executing remote commands. If the remote commands produce any output, the output may be sent along with the result of the commands back to the customer support portal.

Region-specific result service 320 may generate result reports. In some embodiments, results may be generated with formats, graphics, or content, specific to a region. Health data management system 100 may set up, or be in contact with, a result service 320 for each region it interfaces with, or for a result service 320 for one or more regions (e.g., in scenarios involving a network of hospitals, healthcare providers, or a geographical region). A result service 320 may store one or more pre-determined result settings (e.g., result formats, graphics, content, etc.) for its respective region. In some cases, the result service 320 may store one or more result reports until retrieval by a result transport service 312. The health data management system 100 and/or the result service 320 may retrieve patient privacy data and pair it with completed medical analyses to create a final result report.

Figure 4:
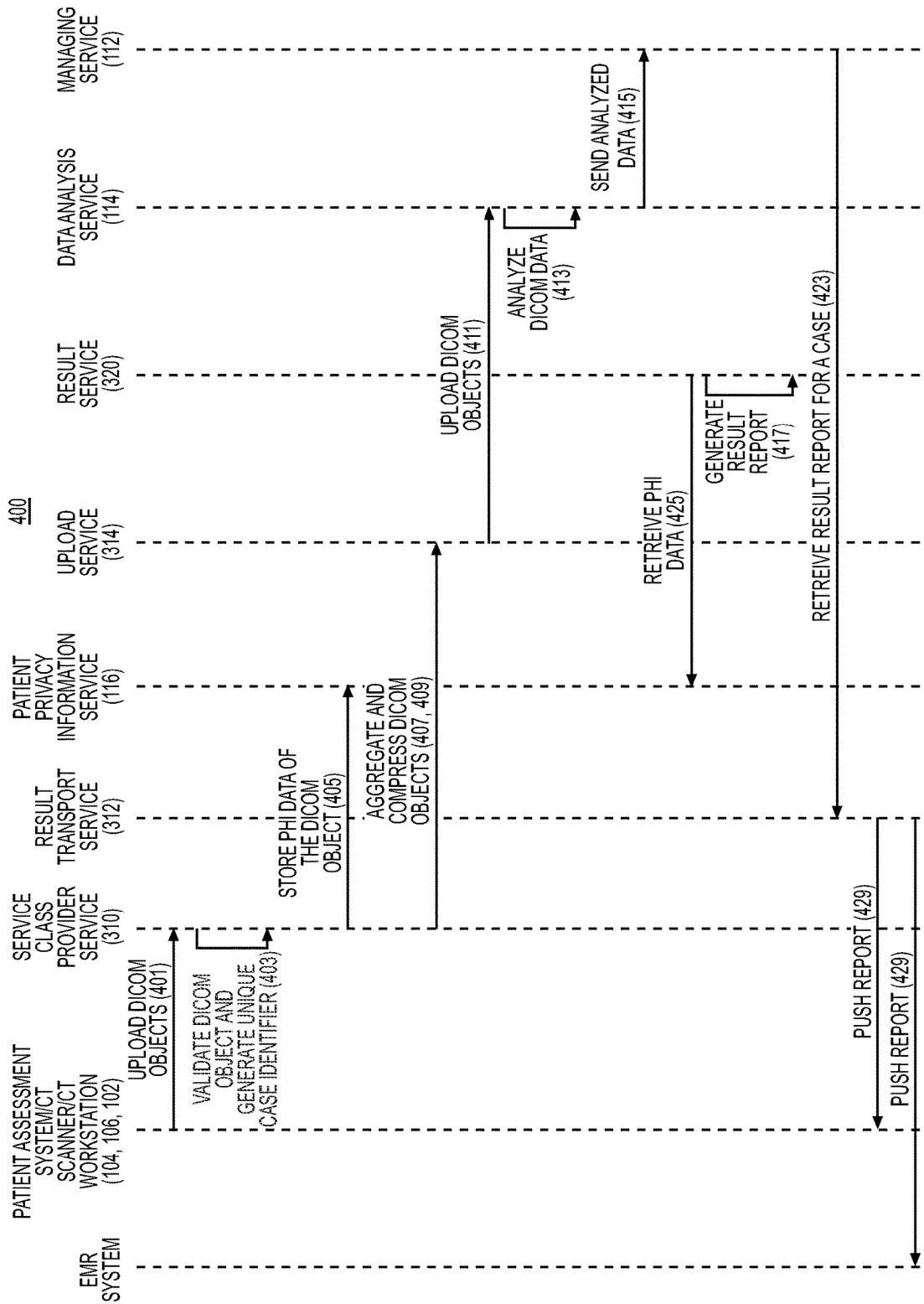
FIG. 4 depicts an exemplary sequence flow of health data through the health data management system 100, according to an exemplary embodiment of the present disclosure.

FIG. 4 depicts an exemplary sequence flow of a method 400 of managing health data using health data management system 100. In an example embodiment, SCP service 310 may detect the availability or uploading of one or more DICOM objects by a hospital computing device (e.g., a CT scanner 104, patient assessment system 106, a CT workstation 102, etc.). As previously discussed, the SCP service 310 may poll one or more hospital computing device(s) to detect when a DICOM object is generated. When a hospital computing device generates or creates a DICOM file, the SCP service 310 may detect the DICOM file (e.g., step 401). In one embodiment, step 403 may include the SCP service 310 generating a unique case for a single case study. The unique case may prepare the detected DICOM object for a case study (e.g., by data analysis service 114). In one embodiment, the SCP service 310 may further generate a unique case identifier for the case.

In one embodiment, SCP service 310 may also validate the DICOM object. For instance, validating the DICOM object may include determining or receiving pre-defined image quality criteria for DICOM objects that may undergo analysis by the data analysis service 114. SCP service 310 may determine whether the received DICOM object meets the pre-defined criteria. If the DICOM object meets the criteria, the SCP service 310 may proceed with other steps of method 400. If the DICOM object does not meet the criteria, SCP service 310 may notify a device of the hospital to re-generate a DICOM object or resubmit the data. The SCP service 310 may further provide the reasons that the DICOM object did not pass validation.

In an exemplary embodiment, the DICOM objects may include patient privacy information (e.g., PHI data). The SCP service 310 may extract the PHI data from the DICOM objects to de-identify the DICOM objects. For example, the SCP service 310 may extract PHI data from the DICOM objects and replace the PHI data with a predefined string and/or the unique case identifier. Additionally, the SCP service 310 may encrypt the PHI data. The PHI data may be stored by a region-specific patient privacy information web service 116 (e.g., step 405). In one embodiment, PHI data of a case may be stored such that the PHI data is associated with the unique case identifier of the case.

In the above illustrated embodiment, the SCP service 310 may detect DICOM objects associated with a single case study. For example, SCP service 310 may detect that multiple DICOM objects are associated with one case study. SCP service 310 may aggregate the multiple DICOM objects for the case study (e.g., step 407). SCP service 310 may further compress aggregated DICOM objects associated with the single case study (e.g., step 409). An upload service 314 may receive the compressed DICOM objects for a case study. The upload service 314 may further upload the one or more compressed DICOM objects associated with a single case study to data analysis service 114 (e.g., step 411). In one embodiment, each case study may have a priority level associated with it. The upload service 314 may push the compressed DICOM objects to a data analysis service 114 according to the priority level of the DICOM object. For example, DICOM objects with a higher priority level may be pushed to the data analysis service 114 before DICOM objects with a lower priority level. The priority level may be dictated by a health care professional when the DICOM object is generated. Alternately or in addition, the priority level may be set based on the hospital computing device from which the DICOM object is received, based on the SCP service 310, based on the data analysis service 114 performing the analysis, etc. The priority level may also be altered at one or more stages/steps of method 400. In one embodiment, the data analysis service 114 may perform a series of computations and image processing to analyze the one or more DICOM objects (e.g., step 413).

In an example embodiment, managing service 112 may receive the one or more analyzed DICOM objects from data analysis service 114 (e.g., step 415). The managing service 112 may verify the data analysis performed by the data analysis service 114. The managing service 112 may verify that all components of the data analysis are completed and sufficient to complete the results report. Managing service 112 or result service 320 may further generate a result report (e.g., step 417). In an alternative embodiment, the managing service 112 may make the analyzed DICOM objects available to an analysis technician. The technician may further verify the analysis and submit the request for generating a result report. Alternately or in addition, the technician may further edit the analysis of the result report. For example, managing service 112 may provide one or more prompts for the technician to verify the analysis. In one scenario, managing service 112 may generate various reporting options for a technician to select from. The options may include one or more pins, displays, views, charts, comparisons, etc., where a technician may select a combination of the offered options to finalize a report of the analyzed DICOM data.

Result transport service 312 may receive a result report from the managing service 112 (e.g., step 419). The result report may include a PDF of analysis results, an interactive model with various displays or views, etc. In one embodiment, the model may include a 3D anatomic model that a user may manipulate to see different parts of the analysis. For example, an analysis may generate a blood flow model through the 3D anatomic model. Various embodiments of diagnostic analyses using image reconstructions and anatomic models are disclosed, for example, in U.S. Pat. No. 8,315,812 issued Nov. 20, 2012, entitled "Method and System for Patient-Specific Modeling of Blood Flow," which is incorporated by reference in its entirety. The report may include a surface model, graph, chart, color-coding, indicators, interactive displays, alerts, signals, or any known graphical objects. Various embodiments of graphical representations and displays are disclosed, for example, in U.S. Pat. No. 8,706,457 issued Apr. 22, 2014, entitled "Method and System for Providing Information from a Patient-Specific Model of Blood Flow," which is incorporated by reference in its entirety. In one embodiment, the result transport service 312 may store the result report at result database (e.g., step 421). Each of the reports may include an associated unique case identifier.

In an example embodiment, the SCP service 310 or managing service 112 may receive a request to retrieve a result report, and in response, a result report may be conveyed by the result transport service 312 (e.g., step 423). The request may be conveyed by a web interface (e.g., using RESTful API 206). In one embodiment, the request may include a unique case identifier.

In an example embodiment, the SCP service 310 may associate patient privacy data with a retrieved result report. For example, SCP service 310 may detect a unique case identifier of a report and determine patient privacy data corresponding to the unique case identifier. In one such scenario, result service 320 or SCP service 310 may transmit a unique case identifier to the patient privacy information web service 116 and request stored PHI data from the patient privacy information web service 116 that corresponds to the unique case identifier (e.g., step 425). The patient privacy information web service 116 may retrieve the encrypted PHI data for a unique case identifier from the relational database 322 and send the PHI data to the SCP service 310. The SCP service 310 may further decrypt the PHI data and update the retrieved result report with decrypted PHI data (e.g., step 427). The SCP service 310 may push the result report to a device or interface where a user may access the report (e.g., step 429). While the above embodiment describes the patient privacy information as PHI data, the embodiment may be applied to any form of patient privacy information.

Figure 5:
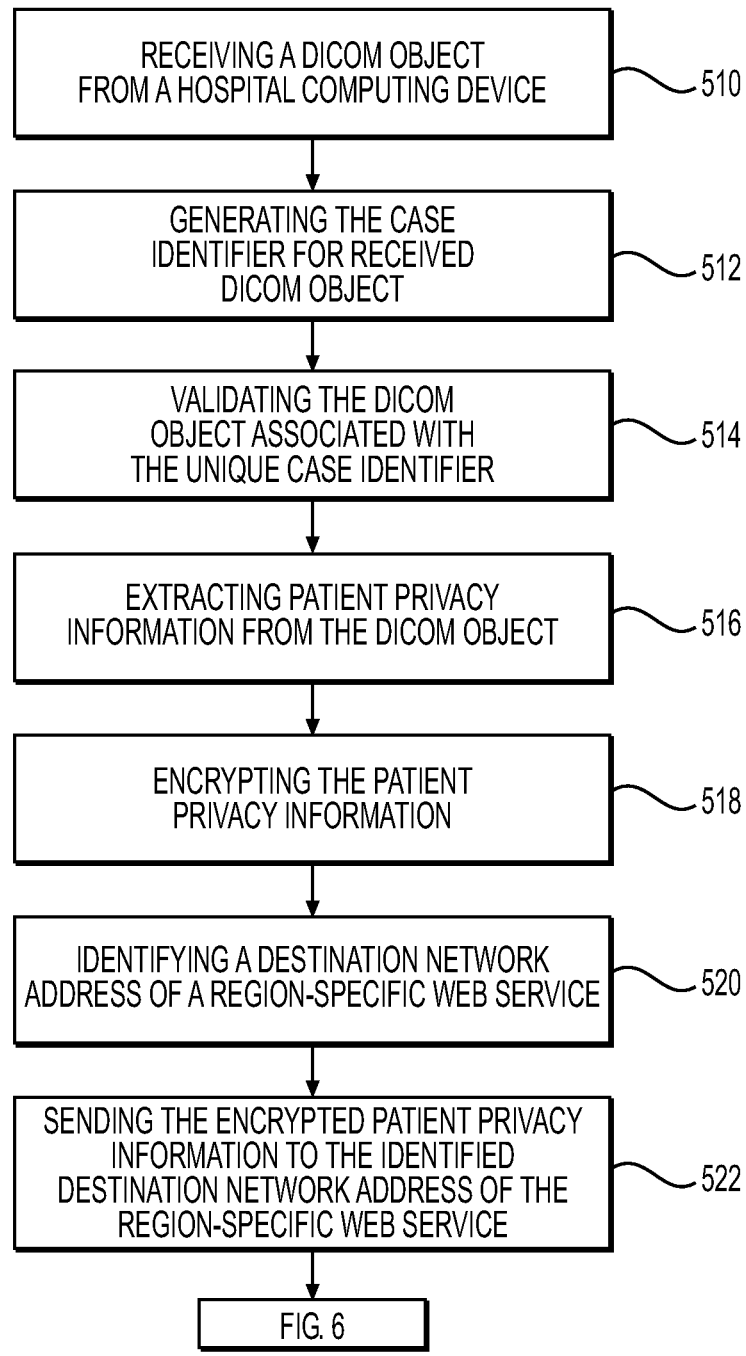
FIG. 5 is a flow diagram of an exemplary method of managing health data, according to an exemplary embodiment of the present disclosure.

FIG. 5 is a flow diagram 500 of an exemplary method of managing health data, according to an exemplary embodiment of the present disclosure. In operation 510, health data may be received at the health data management system 100 from a hospital computing device. Health data in operation 510 may be in Digital Imaging and Communications in Medicine (DICOM) format. The hospital computing device may include a CT scanner 104, patient assessment system 106, or a CT workstation 102, as shown in FIG. 1.

In an example embodiment, the health data management system 100 may generate a unique case identifier for the received health data (e.g., DICOM object) as per operation 512. In operation 514, health data management system 100 may validate the health data (e.g., DICOM object). For example, a DICOM object may be invalid if the DICOM object is missing a DICOM image, if DICOM image size is outside of a defined range, or if the DICOM image does not meet defined quality requirements. In an alternative embodiment, the health data management system 100 may send a message to a hospital computing device as a result of determining that the received DICOM object is invalid. For example, the health data management system 100 may prompt a re-sending of a DICOM object and/or provide a notification that the received DICOM object is invalid and another DICOM object should be generated.

In operation 516, the health data management system 100 may strip patient privacy information from the validated DICOM object. Exemplary patient privacy information may include information that can link the DICOM object to a patient, e.g., a patient's name, date of birth, phone number, address, email address, social security number, etc. In an example embodiment, the health data management system 100 may further encrypt the extracted patient privacy information by de-identifying each piece of patient privacy information using a one-way cryptographic function (e.g., operation 518).

In operation 520, the health data management system 100 may identify a destination network address of a region-specific web service to send the encrypted patient privacy information. In an example embodiment, to identify a region-specific web service, the health data management system 100 may provide network parameters of the hospital computing device associated with the received DICOM object to a Web Application Firewall (WAF) service to geo-locate the hospital computing device. The WAF service may re-direct the health data management system 100 to a location-specific Application Programming Interface (API). The health data management system 100 may access the location-specific API and retrieve a network address of the region-specific web service (e.g., patient privacy information web service 116) for managing and storing the patient privacy data. In operation 522, the health data management system 100 may send the patient privacy information to the identified destination network address of the region-specific web-service (e.g., of operation 520). In an example embodiment, the health data management system 100 may send the encrypted patient information along with a unique case identifier to the identified location-specific web service.

Figure 6:
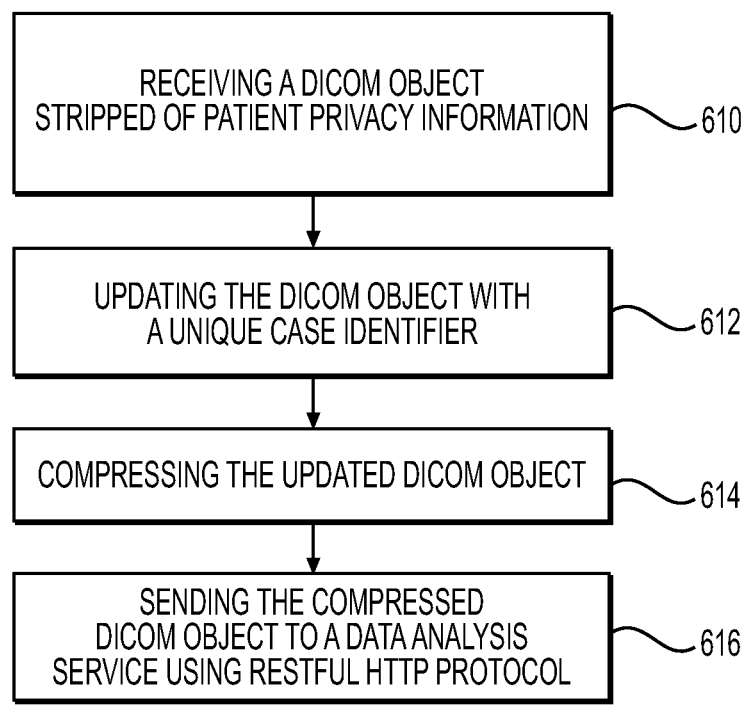
FIG. 6 is a flow diagram of an exemplary method of sending health data for analysis cross-borders, according to an exemplary embodiment of the present disclosure.

FIG. 6 is a flowchart 600 that further depicts transferring anonymized data to a cloud platform for analysis, according to an exemplary embodiment of the present disclosure. In operation 610, the health data management system 100 may receive a DICOM object stripped of patient privacy information. The health data management system 100 may update the anonymous DICOM object (without patient privacy information) to include the unique case identifier (e.g., operation 612). For example, the DICOM object may have a header that may be updated to include the unique case identifier. (In alternative embodiments, the unique case identifier may simply be sent along with the DICOM object to the data analysis service 114, rather than as part of the DICOM object itself.) In operations 614 and 616, the health data management system 100 may compress the DICOM object and send the compressed DICOM object to data analysis service 114. In one embodiment, the compressed DICOM object may be sent using REST HTTP protocol.

Figure 7:
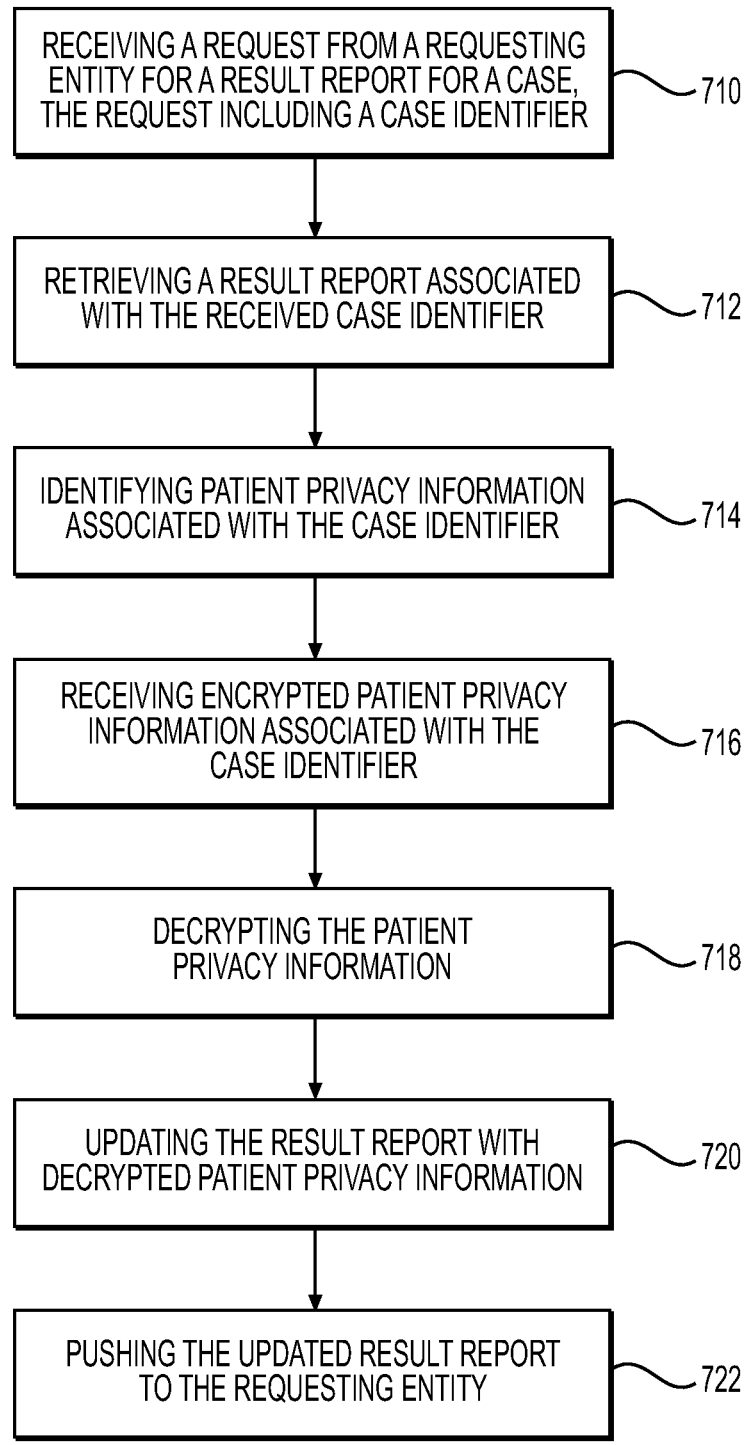
FIG. 7 is a flow diagram of an exemplary method of receiving a health data analysis report according to an exemplary embodiment of the present disclosure.

FIG. 7 is a flowchart 700 of receiving a result report of the analyzed health data, according to an exemplary embodiment of the present disclosure. The method flowchart 700 may be performed by the health data management system 100, the data analysis service 114, or any combination of the components shown in FIG. 1. In an example embodiment, a user (e.g., a hospital technician) may request a report for a case. For example, the user may access a web application (e.g., an online portal) and provide a unique case identifier. The web application may covey the request to the health data management system 100. As per operation 710, the health data management system 100 may receive the request for result report from the user through a HTTP Protocol, where the request may provide the unique case identifier.

In one embodiment, completed reports may be stored in a database. The completed reports may include a unique case identifier. In one embodiment, step 712 may include retrieving a result report that corresponds to the received unique case identifier. In one embodiment, step 714 may include identifying patient privacy information associated with the completed report. For example, step 714 may include providing a patient privacy information data service (e.g., patient privacy information web service 116) with the unique case identifier. Step 716 may include receiving patient privacy information associated with the unique case identifier. The patient privacy information may be encrypted. In one example, a user may provide a request including patient information that may be part of the patient privacy information. The database may identify a unique case identifier associated with the patient information, and a report associated with the unique case identifier may be retrieved. The report may then be associated with the corresponding patient privacy information. In one embodiment, step 718 may include decrypting the received patient privacy information and step 720 may include updating the result report to include decrypted patient privacy information.

Step 722 may include pushing the updated result report to the requesting entity. The updated result report may be sent to the requesting entity using standard HTTP protocols and a web interface (e.g., step 722). In an alternate embodiment, a result report may be pushed to a hospital computing system (e.g., patient assessment system 106 or CT workstation 102) when the result reports are completed. For example, health data management system 100 may check managing service 112 for the cases in a "COMPLETED" state, where report documents have not yet been delivered. (The "COMPLETED" state may indicate that analysis is complete and a report is either already generated, or a report can be generated based on the analysis results.) For every undelivered "COMPLETED" case, the health data management system 100 may download preconfigured reports or report settings (e.g., preferred report formats or styles, as set by the hospital or requesting entity). The result service 320 may wrap the PDF document, based on configuration, either as a DICOM encapsulated PDF object or as a HL7 message, and push the object (DICOM/HL7) to an appropriate pre-configured destination. Configuration is described in further detail at FIGS. 8A-8C. For example, in a scenario involving pushing a health data report to at least one of a hospital computing device, hospital electronics records server, and/or pre-configured destination network address, a HL7 standard message may be sent to the at least one hospital computing device, hospital electronics records server and pre-configured destination network address. The HL7 standard message may contain a uniform resource locator (URL) to the report.

In one embodiment, the health data management system 100 may act as a SCP service that receives and stores a report as an encapsulated PDF DICOM object. The health data management system 100 may then further issue a push command for the receiver to receive the report. If the health data management system 100 is configured to push report(s) to a HL7 engine/broker, the health data management system 100 may act as an HL7 client, sending the reports as HL7 messages to the engine/broker or requesting entity (e.g., hospital). In one embodiment, the health data management system 100 may further identify metadata associated with a complete report, e.g., insurance information, insurance plan coverage, report completion time, report priority, relation of the analysis to prior analyses, etc. Such metadata may be aggregated to inform uses of the completed report by the requesting entity.

Figure 8A:
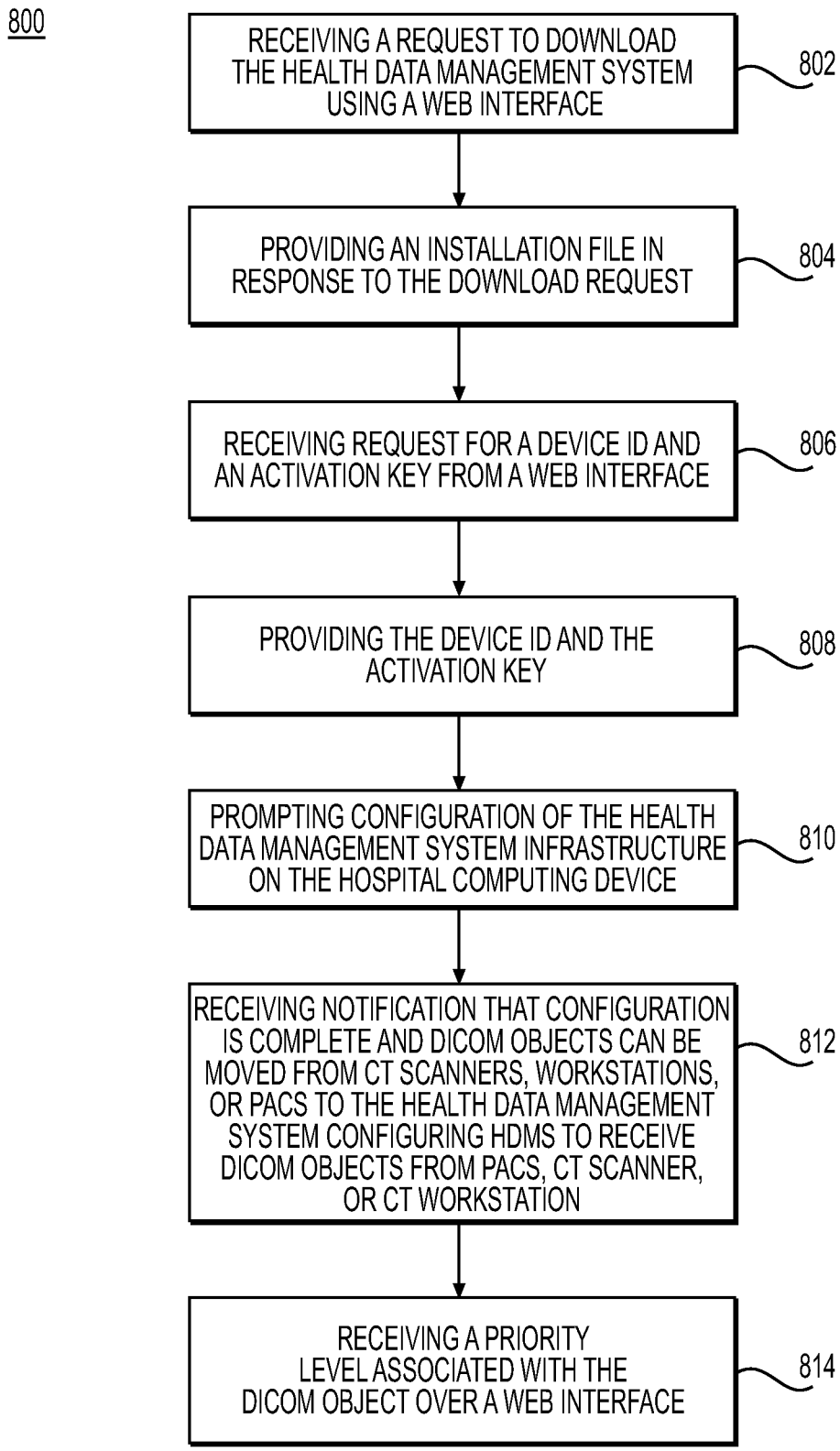
FIG. 8A is a flow diagram of an exemplary method of installing health data management system 100 of FIG. 1, according to an exemplary embodiment of the present disclosure.

FIG. 8A is an exemplary flowchart 800 showing deployment of a health data management system 100 in a customer network, according to an exemplary embodiment of the present disclosure. In an example embodiment, a customer may include a clinic or a hospital, and a customer network may include a network operating within the clinic or hospital. The health data management system 100 may be deployed on a clinic/hospital machine. In one embodiment, managing service 112 may receive a request to download the health data management system 100 (e.g., step 802). For example, a site administrator may send a request over a web interface to data analysis vendor's managing service 112 to enroll the hospital as a customer of the vendor. The managing service 112 may provide an installation (e.g., an open virtual appliance or application (OVA)) file in response to the download request (e.g., step 804). In an example embodiment, to establish the health data management system 100 infrastructure, an OVA (open virtual appliance or application) file may be installed on a hospital computing device. The OVA file may be deployed into a virtual environment on the hospital computing device using a virtual machine (VMware) client. The OVA file may contain components such as operating system (e.g., customized CentOS Linux distribution), the health data management system 100 software, and configuration details for a virtual hardware (e.g., RAM and CPU reservations and storage requirements, NIC (Network Interface Card) settings, etc.).

The managing service 112 may further provide the site administrator with a device identification and an activation key for the health data management system 100 in response to a request for activation of the health data management system 100 (e.g., steps 806 and 808). In one embodiment, the managing service 112 may provide the device identification and/or the activation key via a web interface.

In one embodiment, the OVA file may be deployed in the hospital system and the health data management system 100 may be booted as a new virtual machine. The health data management system 100 may include a console accessible by the site administrator for configuring network parameters for the health data management system 100, DICOM settings, communication port(s), as well as for retrieving the device identification and activation key from the managing service 112. In an alternative embodiment, the activation key may be emailed to the site administrator to be entered while configuring the health data management system 100. In an example embodiment, after deploying OVA file, the site administrator may configure the network parameters for the virtual machine, DICOM Application Entity (AE) title, and communication ports to enable CT scanner 104, CT workstation 102, and patient assessment system 106 to move DICOM studies to the health data management system 100 (e.g., step 810). In one embodiment, managing service 112 may provide settings for the configurations that may establish the health data management system infrastructure at the hospital.

In one embodiment, the site administrator may configure CT scanner 104, CT workstation 102, and patient assessment system 106 with the health data management system 100 DICOM Application Entity (AE) title and communication port(s). In one embodiment, the managing service 112 may receive a notification that configuration is complete and CT scanner 104, CT workstation 102, and patient assessment system 106 can move DICOM studies to the health data management system 100 (e.g., step 812).

In an example embodiment, the hospital clinician or admin may enter priority for the DICOM object using a web interface (e.g., step 814). In an alternative embodiment, the priority may be set automatically according to the location of the hospital device in the hospital, DICOM object source CT scanner 104, CT workstation 102 or patient assessment system 106. The priority may be sent to the managing service 112 using HTTP protocol. The managing service 112 may store and maintain the priority of the DICOM object or a case study, and further provide the result reports in an order or urgency according to the priority.

Figure 8B:
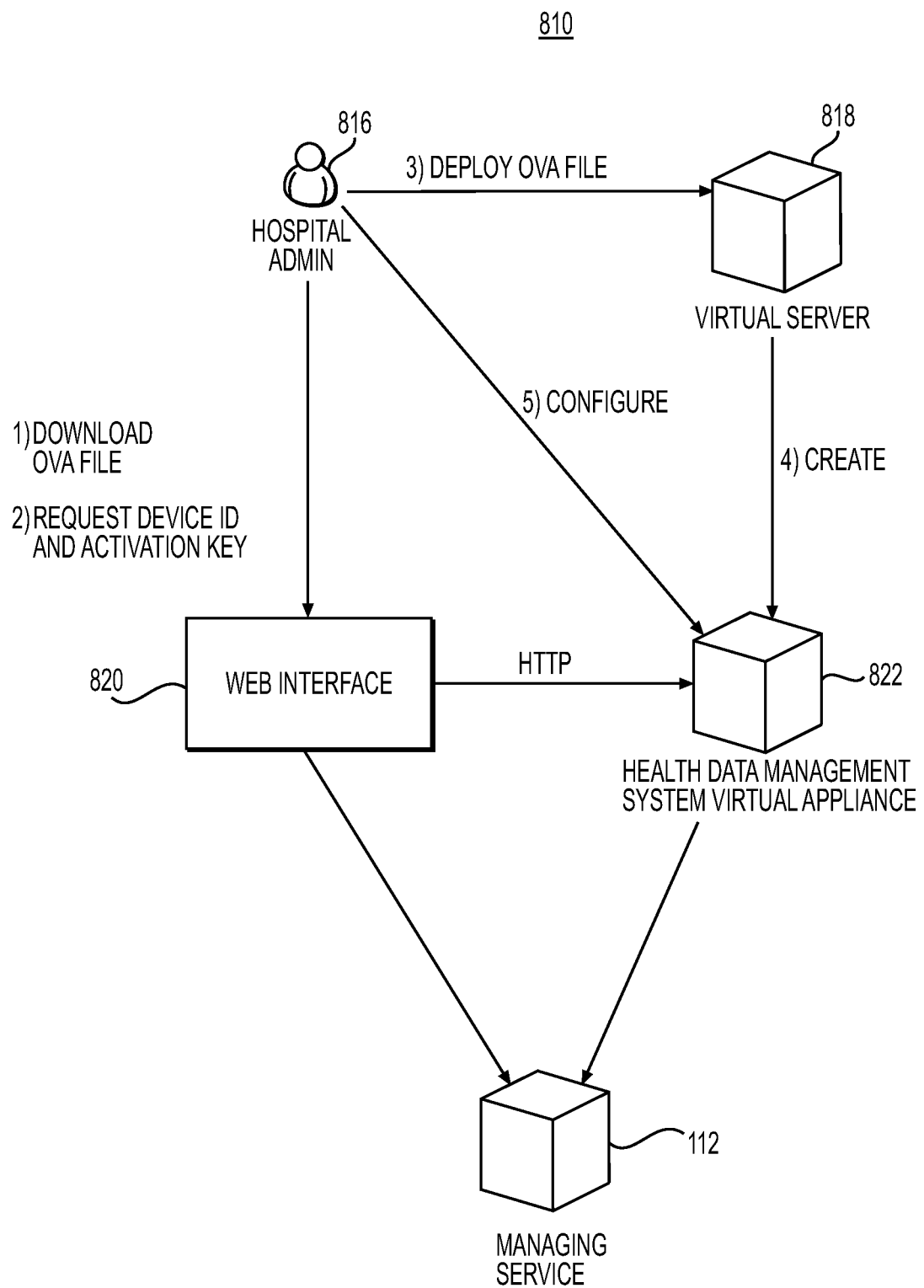
FIG. 8B is an exemplary schematic block diagram and dataflow of installation of the health data management system 100 of FIG. 1, according to an exemplary embodiment of the present disclosure.

FIG. 8B depicts data flow 810 for installing the health data management system 100. As shown in step 1, the hospital site administrator 816 may request to download an OVA file containing the health data management system 100. The request may be received at a web interface 820 (e.g., of a managing service 112 for a data analysis service 114). Hospital site administrator 816 may further request a device identification and an activation key as part of the installation process (step 2). The managing service 112 may provide the OVA file, device identification, and activation key via the web interface 820.

In one embodiment (e.g., step 3), the hospital site administrator 816 may deploy the OVA file on a virtual machine server (e.g., virtual server 818). In an example embodiment, step 4 may include deploying a health data management system virtual appliance 822 on a virtual machine host. In one embodiment, deployment may include the hospital site administrator 816 selecting the virtual appliance 822 from a virtual machine client inventory menu, starting the virtual appliance 822, and initiating the virtual appliance machine console view. The hospital site administrator 816 may further configure the health data management system virtual appliance 822 (e.g., step 5) to enable the health data management system virtual appliance 822/heath data management system 100 to receive health data from CT scanner 104, CT workstation 102, or patient assessment system 106.

In an example embodiment, the health data management system 100 may be hosted on a Linux 64-bit Operating System. Upon startup, a configuration menu may be displayed on the Linux console. The access of the user of the console may include a menu to provide protection against the misuse and reverse-engineering of the health data management system 100. The menu may allow the user to configure the hostname and network parameters for the device, as well as its DICOM Application Entity (AE) title and communication port.

Figure 8C:
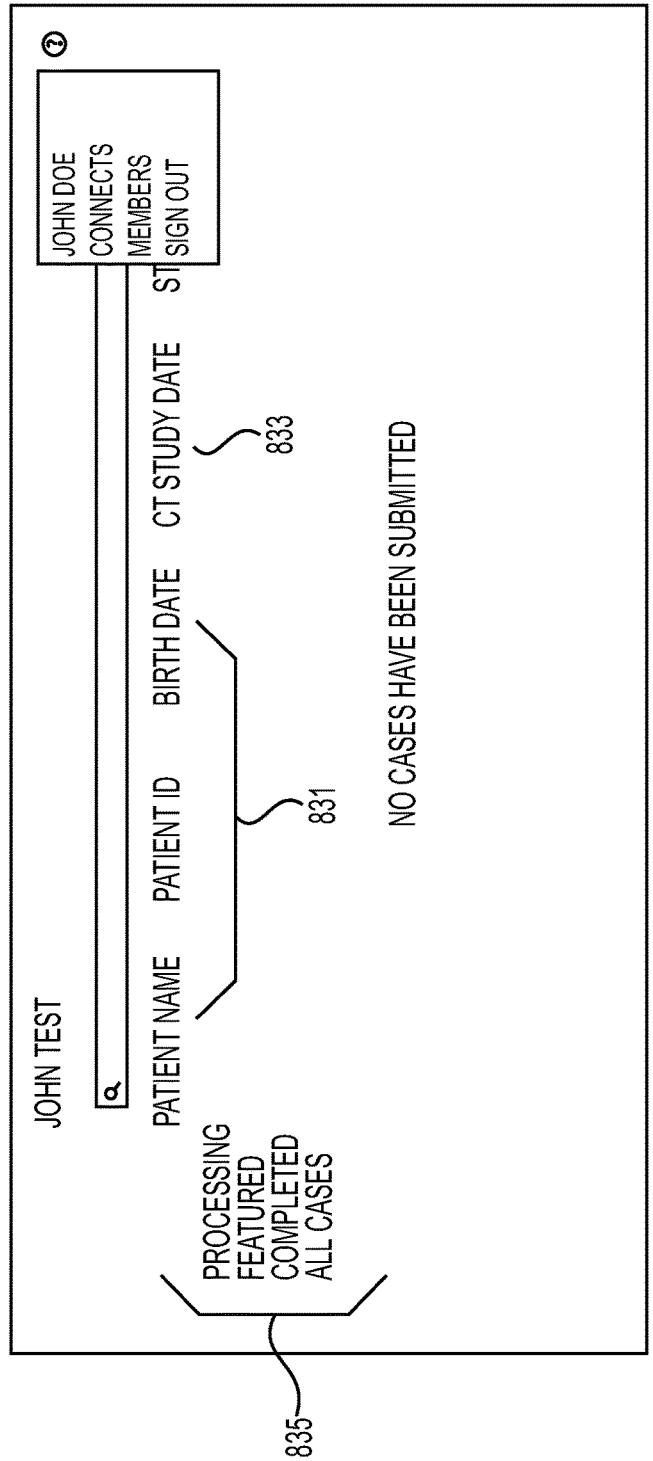
FIG. 8C is screenshot of web interface that allows a hospital admin to configure health data management system 100 of FIG. 1, according to an exemplary embodiment of the present disclosure.

FIG. 8C shows an exemplary web interface 830 once health data management system 100 is configured to receive files from hospital computing device(s). For example, the interface 830 may include information corresponding to a patient 831 and information on the received file (e.g., CT DICOM object) 833. The interface 830 may further include information denoting the status 835 of an analysis (e.g., whether the analysis is processing, completed, or stored (e.g., in "All Cases")). The status 835 may also include analyses or reports that are of particular note (e.g., "featured"). These analyses or reports may be flagged for a medical professional for deeper study or for future reference.

Thus, the present disclosure includes a system and method for analyzing, storing, and managing patient's health data in different geographical regions while preserving patient privacy data. The present disclosure further includes a system and method for sending anonymous health data to an analysis cloud platform outside of the region of the hospital and receiving an analysis result report. Accordingly, data analysis may be provided across regions, while avoiding the transfer of privacy data from one region to another.

Any of the described embodiments may be modified, for example, to include variations of data that may be kept within a region. The disclosed systems and methods may be modified to model and assess any range of changes to circulation. Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming.

It should be appreciated that health data management system 100 may include any type or combination of computing systems, e.g., handheld devices, personal computers, servers, clustered computing machines, and/or cloud computing systems. In one embodiment, health data management system 100 may comprise an assembly of hardware, including a memory, a central processing unit ("CPU"), and/or a user interface. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory.

In one embodiment, users may upload the DICOM objects and retrieve result reports using one or more wired or wireless devices. Devices may include any type of electronic device configured to collect, send, and/or receive data, such as websites and multimedia content, over a network. Devices may include medical devices, e.g., medical imaging devices, medical monitors, etc. Devices may also include one or more mobile devices, smartphones, personal digital assistants ("PDA"), tablet computers or any other kind of touchscreen-enabled device, a personal computer, a laptop, and/or server disposed in communication a network. Each of the devices may have a web browser and/or mobile browser installed for receiving and displaying electronic content received from one or more of web servers. The devices may include client devices that may have an operating system configured to execute a web or mobile browser, and any type of application, e.g., a mobile application. In one embodiment, various devices may be configured with network adapters to communicate data or analyzed reports over a network. Alternatively, or additionally, various may be configured to transmit data or receive analyzed data over a local connection.

The functions of one or more processors associated with one or more cloud-based web services may be provided by a single dedicated processor or by a plurality of processors. Moreover, the processor may include, without limitation, digital signal processor (DSP) hardware, or any other hardware capable of executing software.

All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of managing cross-border health data while preserving patient privacy, the method comprising:

receiving into a temporary storage, via a health data management system in a first geographic region, a plurality of DICOM objects from a hospital computing device for analysis, the hospital computing device being provided in the first geographic region, wherein the DICOM objects pertain to a single case study of a patient in the first geographic region, wherein the DICOM objects include images showing a change in vessel shape over a cardiac cycle of the patient, and wherein the temporary storage is located in the first geographic region;

generating a unique case identifier for the DICOM objects;

validating each received DICOM object of the DICOM objects;

anonymizing each validated DICOM object, wherein anonymizing each validated DICOM object includes:

extracting patient privacy information from the DICOM object, wherein the patient privacy information is stripped from the anonymous DICOM object, determining a geo-location of the hospital computing device, identifying a region-specific web service in the first geographic region, the first geographic region including the geo-location of the hospital computing device, and providing the extracted patient privacy information with the unique case identifier to the identified region-specific web service;

updating the anonymous DICOM objects to include the unique case identifier;

compressing the updated DICOM objects;

providing the compressed DICOM objects to at least one data service(s) located in a second geographic region outside of the first geographic region, the data service being configured to analyze the compressed DICOM objects and generate a 3D model of the patient's heart and/or one or more calculations of blood flow within the vessels;

deleting the DICOM objects from the temporary storage while maintaining the extracted patient privacy information with the identified region-specific web service, wherein deleting the DICOM objects from the temporary storage is performed after providing the compressed DICOM objects to the at least one data service(s) and before receiving a report;

receiving, in the first geographic region and from the second geographic region, the report of the data analyzed by the at least one data service, wherein the report includes the generated 3D model of the patient's heart or the one or more calculations of blood flow; and pairing the report with the extracted patient privacy information.

2. The computer-implemented method of claim 1, wherein the validation of each received DICOM object is based on DICOM image size, positioning of the DICOM image, or image quality associated with the DICOM object.

3. The computer-implemented method of claim 1, wherein the step of anonymizing each received DICOM object is further comprised of:

encrypting the extracted patient privacy information;

wherein providing the extracted patient privacy information to the identified region-specific web service includes providing the encrypted patient privacy information with the unique case identifier to the identified region-specific web service, and the method further comprises maintaining the encrypted patient privacy information within the first geographic region.

4. The computer-implemented method of claim 1, wherein:

determining the geo-location of the hospital computing service includes providing one or more network parameters associated with the hospital computing device to a Web Application Firewall (WAF) service; and identifying the region-specific web service includes retrieving a network address of a region-specific web service using a location-specific Application Programming Interface (API) provided by the WAF service and installed in the first geographic region, wherein the identified region-specific web service is the region-specific web service associated with the retrieved network address.

5. The computer-implemented method of claim 1, further comprising:

receiving a request to download the health data management system on the hospital computing device; and providing an installation file for downloading the health data management system on the hospital computing device.

6. The computer-implemented method of claim 5, further comprising:

configuring the health data management system to receive a DICOM object from at least one of a patient assessment system, a CT Scanner, and a hospital workstation;

receiving a priority of the DICOM object over a web interface, the priority being based on the hospital computing device; and updating the compressed DICOM object based on the received priority.

7. The computer-implemented method of claim 5, further comprising:

creating a virtual machine on the hospital computing device;

deploying the installation file from a virtual machine client; and activating the virtual machine.

8. The computer-implemented method of claim 5, wherein the step of configuring the health data management system is further comprised of:

configuring a host name, one or more network parameters for the hospital computing device, one or more communication ports, a DICOM application entity title, or a combination thereof.

9. The computer-implemented method of claim 1, wherein the report includes a health data report including an interactive view, and the method further comprises:

receiving a request for the health data report in a region-specific defined format;

retrieving the health data report from the data service using the unique case identifier; and pushing the health data report to at least one of a computing device, a hospital electronics records server, or a pre-configured destination network address provided in the first geographic region, wherein pairing the report with the extracted patient privacy information includes:
  retrieving patient privacy information associated with the unique case identifier;
  decrypting the received patient privacy information; and
  updating the retrieved health data report to include the decrypted patient privacy information.

10. The computer-implemented method of claim 9, wherein the health data report is pushed as a Health Level Seven International (HL7) message, DICOM file, or as a portable document format (PDF) object.

11. The computer-implemented method of claim 1, wherein the hospital computing device is at least one of a patient assessment system, an imaging modality, and a hospital workstation.

12. The method of claim 1, wherein the plurality of DICOM objects include images showing coronary arteries, the data service is configured to determine blood flow within coronary arteries and Fractional Flow Reserve values, and the 3D model includes an interactive 3D model of the coronary arteries showing the determined Fractional Flow Reserve values.

13. The method of claim 1, wherein providing the compressed DICOM objects to the at least one data service(s) includes pushing the DICOM objects to the at least one data service(s), and the method further comprises:
  receiving a secondary plurality of DICOM objects for a secondary case study of at least one secondary patient, wherein the secondary case study has a lower priority level than the single case study;
  generating a secondary unique case identifier for the secondary plurality of DICOM objects;
  validating each received secondary DICOM object;
  anonymizing each validated secondary DICOM object;
  updating the anonymous secondary DICOM objects to include the secondary unique case identifier;
  compressing the updated secondary DICOM objects;
  after pushing the compressed DICOM objects associated with the single case study to the at least one data service(s), pushing the compressed secondary DICOM objects to the at least one data service(s); and
  providing a status of the single case study and the secondary case study.

14. The method of claim 1, further comprising providing a status of an analysis of the compressed DICOM objects performed by the at least one data service.

15. The method of claim 1, wherein the extracting patient privacy information includes information related to a service provider, an insurance policy, or annotations from image acquisition, and further comprising:
  providing billing functions based on the service provider or the insurance policy, and/or
  performing a reconstruction on one or more DICOM objects or discarding one or more DICOM objects based on the annotations.

16. The method of claim 1, wherein deleting the DICOM objects from the temporary storage occurs a predetermined time after providing the compressed DICOM objects to the at least one data service(s).

17. The method of claim 16, wherein the predetermined time is zero.

18. A system for managing cross-border health data while preserving patient privacy, the system comprising:
  one or more data storages devices storing instructions of managing cross-border health data while preserving patient privacy; and
  one or more processors configured to execute the instructions to perform a method including:
    receiving into a temporary storage, via a health data management system in a first geographic region, a plurality of DICOM objects from a hospital computing device for analysis, the hospital computing device being provided in the first geographic region, wherein the plurality of DICOM objects pertain to a single case study of a patient in the first geographic region, wherein the DICOM objects include images showing a change in vessel shape over a cardiac cycle of the patient, and wherein the temporary storage is located in the first geographic region;
    generating a unique case identifier for the plurality of DICOM objects;
    validating each received DICOM object;
    anonymizing each validated DICOM object, wherein anonymizing each validated DICOM object includes:
      extracting patient privacy information from the DICOM object, wherein the patient privacy information is stripped from the anonymous DICOM object,
      determining a geo-location of the hospital computing device,
      identifying a region-specific web service in the first geographic region, the first geographic region including the geo-location of the hospital computing device, and
      providing the extracted patient privacy information with the unique case identifier to the identified region-specific web service;
    updating the anonymous DICOM objects to include the unique case identifier;
    compressing the updated DICOM objects;
    providing the compressed DICOM objects to at least one data service(s) located in a second geographic region outside of the first geographic region, the data service being configured to analyze the compressed DICOM objects and generate a 3D model of the patient's heart and/or one or more calculations of blood flow within the vessels;
    deleting the DICOM objects from the temporary storage while maintaining the extracted patient privacy information with the identified region-specific web service, wherein deleting the DICOM objects from the temporary storage is performed after providing the compressed DICOM objects to the at least one data service(s) and before receiving a report;
    receiving, in the first geographic region and from the second geographic region, the report of the data analyzed by the at least one data service, wherein the report includes the generated 3D model of the patient's heart and/or the one or more calculations of blood flow; and
    pairing the report with the extracted patient privacy information.

19. A non-transitory computer readable medium for use on a computer system containing computer-executable programming instructions for performing a method for managing cross-border health data while preserving patient privacy, the method comprising:
  receiving into a temporary storage, via a health data management system in a first geographic region, a plurality of DICOM objects from a hospital computing device for analysis, the hospital computing device being provided in the first geographic region, wherein the plurality of DICOM objects pertain to a single case study of a patient in the first geographic region, wherein the DICOM objects include images showing a change in vessel shape over a cardiac cycle of the patient, and wherein the temporary storage is located in the first geographic region;

generating a unique case identifier for the plurality of DICOM objects;

validating each received DICOM object;

anonymizing each validated DICOM object, wherein anonymizing each validated DICOM object includes:
  extracting patient privacy information from the DICOM object, wherein the patient privacy information is stripped from the anonymous DICOM object,
  determining a geo-location of the hospital computing device,
  identifying a region-specific web service in the first geographic region, the first geographic region including the geo-location of the hospital computing device, and
  providing the extracted patient privacy information with the unique case identifier to the identified region-specific web service;

updating the anonymous DICOM objects to include the unique case identifier;

compressing the updated DICOM objects; providing the compressed DICOM objects to at least one data analysis web service(s) located in a second geographic region outside of the first geographic region, the data service being configured to analyze the compressed DICOM objects and generate a 3D model of the patient's heart and/or one or more calculations of blood flow within the vessels;

deleting the DICOM objects from the temporary storage while maintaining the extracted patient privacy information with the identified region-specific web service, wherein deleting the DICOM objects from the temporary storage is performed after providing the compressed DICOM objects to the at least one data service (s) and before receiving a report;

receiving, in the first geographic region and from the second geographic region, the report of the data analyzed by the at least one data service, wherein the report includes the generated 3D model of the patient's heart and/or the one or more calculations of blood flow; and pairing the report with the extracted patient privacy information.

20. The non-transitory computer readable medium of claim 19, wherein:

determining the geo-location of the hospital computing service includes providing one or more network parameters associated with the hospital computing device to a Web Application Firewall (WAF) service; and identifying the region-specific web service includes retrieving a network address of a region-specific web service using a location-specific Application Programming Interface (API) provided by the WAF service, wherein the identified region-specific web service is the region-specific web service associated with the retrieved network address.

* * * * *